(12) United States Patent
Bryske et al.

(10) Patent No.: US 9,839,597 B2
(45) Date of Patent: Dec. 12, 2017

(54) COMBATING DENTINE HYPERSENSITIVITY WITH A NON-IONIC POLYMER

(75) Inventors: Karin Maria Bryske, Åkarp (SE); Mark Ieuan Edwards, Surrey (GB); Louise Gracia, Surrey (GB); Simon King, Surrey (GB); Björn Olof Lindman, Villands Vånga (SE)

(73) Assignee: Glaxo Group Limited, Brentford, Middlesex (GB)

( * ) Notice: Subject to any disclaimer, the term of this patent is extended or adjusted under 35 U.S.C. 154(b) by 0 days.

(21) Appl. No.: 14/008,108

(22) PCT Filed: Mar. 28, 2012

(86) PCT No.: PCT/EP2012/055451
§ 371 (c)(1),
(2), (4) Date: Sep. 27, 2013

(87) PCT Pub. No.: WO2012/130863
PCT Pub. Date: Oct. 4, 2012

(65) Prior Publication Data
US 2014/0023596 A1    Jan. 23, 2014

(30) Foreign Application Priority Data

Mar. 30, 2011 (GB) .................................. 1105408.7

(51) Int. Cl.
*A61K 8/73* (2006.01)
*A61Q 11/00* (2006.01)
*A61K 6/00* (2006.01)

(52) U.S. Cl.
CPC ............ *A61K 8/731* (2013.01); *A61K 6/0017* (2013.01); *A61Q 11/00* (2013.01); *A61K 2800/5422* (2013.01)

(58) Field of Classification Search
USPC ................................................ 424/400, 434
See application file for complete search history.

(56) References Cited

U.S. PATENT DOCUMENTS

| 3,954,962 | A | * | 5/1976 | Prussin | 424/49 |
| 5,104,644 | A | * | 4/1992 | Douglas | 424/53 |
| 5,496,541 | A | * | 3/1996 | Cutler | A61K 8/63 424/401 |
| 5,700,478 | A | * | 12/1997 | Biegajski et al. | 424/434 |
| 2007/0190081 | A1 | * | 8/2007 | Narui et al. | 424/400 |
| 2010/0021508 | A1 | | 1/2010 | Hausmanns | |

FOREIGN PATENT DOCUMENTS

| JP | 2009-242346 | * 10/2009 | ............ A61K 31/14 |
| WO | WO 1996/06597 A1 | 3/1996 | |
| WO | WO 2004/045446 A1 | 6/2004 | |

OTHER PUBLICATIONS

Carlsson A. et al.: *Thermal Gelation of Nonionic Cellulose Ethers and Ionic Surfactants in Water*, Colloids and Surfaces, Elsevier, Amsterdam, NL. vol. 47, 1, Jan. 1990 pp. 147-165.

* cited by examiner

*Primary Examiner* — Walter Webb
(74) *Attorney, Agent, or Firm* — Nora L. Stein

(57) ABSTRACT

An oral care composition which is a liquid at or below room temperature and which forms a two-phase cloudy system at body temperature and wherein the composition comprises a water-soluble non-ionic polymer, such as HPC, having a cloud point in the composition at a temperature no higher than about 38° C., for combating (i.e. helping to prevent, inhibit and/or treat) dentinal hypersensitivity.

9 Claims, No Drawings

COMBATING DENTINE HYPERSENSITIVITY WITH A NON-IONIC POLYMER

This application is a 371 national phase entry of International Application No. PCT/EP2012/055451, filed Mar. 28, 2012, which claims the priority of GB Application No. GB 1105408.7 filed Mar. 30, 2011, which is incorporated herein in its entirety.

FIELD OF THE INVENTION

The present invention relates to oral care compositions comprising a non-ionic polymer and their use in combating dentine hypersensitivity.

BACKGROUND OF THE INVENTION

Dentine hypersensitivity is a common but painful condition affecting 18-42% of the adult population and has been defined as "short, sharp pain arising from exposed dentine in response to stimuli, typically thermal, cold, evaporative, tactile, osmotic or chemical which cannot be ascribed to any other form of dental defect or pathology" (*Int. Dent. J.* 2002; 52: 367-375). The primary origin is generally agreed to result from the exposure of dentine following either loss of the protective enamel layer or via gum recession.

The most pronounced morphological characteristic of human dentine is its tubular structure. Dentine tubules have diameters in the order of several micrometers and connect the pulp to the enamel dentine junction. In a healthy subject, these tubules are filled with fluid. It is postulated that this dental fluid plays an active role in the transmission of pain stimuli across the dentine to the underlying neurons. This widely-accepted theory, known as the hydrodynamic theory, states that when the dentine tubules become exposed to the environment, external stimuli elicit a displacement of the dentinal fluid, which, in turn, stimulates mechanoreceptors in the pulp. The movement of fluid through the narrow tubules irritates cells in the vicinity of the base of the tubules, including odontoblasts, pulpal neurons, and even subodontoblastic blood vessels. Several researchers have shown that the fluid movements result in the release, from the pulpal nerves, of calcitonin gene-related peptide, which generates a local neurogenic inflammatory condition.

There are two categories of therapy for the treatment of dentine hypersensitivity based upon two modes of action. The first category, nerve-depolarising agents, are pharmaceutical agents such as potassium nitrate which function by interfering with neural transduction of the pain stimulus.

The second category, known as occluding agents, function by physically blocking the exposed ends of the dentinal tubules, thereby reducing dentinal fluid movement and reducing the irritation associated with the shear stress described by the hydrodynamic theory.

The occlusion approach typically involves treating the tooth with a chemical or physical agent that creates a deposition layer within or over the dentine tubules. This layer mechanically occludes the tubules and prevents or limits fluid movement within the tubule to such an extent that stimulation of the neuron is not achieved. Examples of occlusion actives include among others, calcium salts, oxalate salts, stannous salts, glasses, inorganic oxide particles e.g. $SiO_2$, $Al_2O_3$ and $TiO_2$ and polymers e.g. methylmethacrylate based varnishes.

U.S. Pat. No. 5,270,031 (Block) relates to water soluble or water swellable polymers with functional groups that are capable of bearing one or more charged groups in an aqueous solution having desensitising properties. Such polymers can be anionic, cationic or amphoteric. One example of an anionic functional group is the carboxylate group which is found in polymers such as polyacrylic acid, copolymers of acrylic acid and maleic acid, copolymers of methacrylic acid and acrylic acid, and copolymers of alkyl vinyl ethers and maleic acid or anhydride.

U.S. Pat. No. 5,885,551 (Block) relates to a method of treating dentinal hypersensitivity by administering alginic acid or an alginate in an oral care composition.

U.S. Pat. No. 6,096,292 (Block) relates to the use of a superabsorbent acrylic polymer as a desensitising agent.

U.S. Pat. No. 6,241,972 (Block) relates to compositions and their use in treating dentinal hypersensitivity comprising a copolymer having repeated units of a hydrophilic monomer such as a carboxylic acid, a dicarboxylic acid or a dicarboxylic acid anhydride and a hydrophobic monomer consisting of an alpha-olefin having at least eight carbon atoms, full and partially hydrolysed forms thereof and full and partial salts thereof.

Despite the above proposals, there remains a need for alternative treatments for alleviating dentine hypersensitivity.

SUMMARY OF THE INVENTION

The present invention is directed to the provision of a composition for combating (i.e. helping to prevent, inhibit and/or treat) dentinal hypersensitivity. A first aspect of the present invention provides an oral care composition for combating dentine hypersensitivity which is a liquid at or below room temperature and which forms a two-phase cloudy system at body temperature and wherein the composition comprises a water-soluble non-ionic polymer having a cloud point in the composition at a temperature no higher than about 39° C., suitably in the range from about 32° to about 38° C. In one embodiment the non-ionic polymer is hydroxypropyl cellulose.

It has now been found that dentine hypersensitivity may be alleviated by an aqueous solution of a non-ionic polymer wherein the polymer in the solution has a cloud point at or below a temperature encountered in the oral cavity. Whilst not being bound by any theory, it is believed that when the solution is introduced to the mouth, the non-ionic polymer precipitates and then occludes the dentinal tubules.

In one aspect of the invention there is provided an oral care composition comprising a water-soluble non-ionic polymer having a cloud point in the composition at a temperature no higher than about 38° C., which is a liquid at or below room temperature and which forms a two-phase cloudy system at body temperature, and wherein the composition is useful in combating dentine hypersensitivity.

In an alternative aspect there is provided a method for combating dentine hypersensitivity comprising administering to an individual in need thereof an oral care composition comprising a water-soluble non-ionic polymer having a cloud point in the composition at a temperature no higher than about 38° C., which is a liquid at or below room temperature and which forms a two-phase cloudy system at body temperature.

DETAILED DESCRIPTION OF THE INVENTION

A composition according to the invention comprises a water-soluble non-ionic polymer wherein the polymer has a cloud point in the composition at or below a temperature encountered in the oral cavity. Suitable non-ionic polymers for use in the invention include water-soluble non-ionic cellulose derivatives for example non-ionic water-soluble cellulose ethers such as methyl cellulose (MC), methyl hydroxyethyl cellulose (MHEC), methyl hydroxypropyl cellulose (MHPC), ethyl hydroxyethyl cellulose (EHEC) and hydroxypropyl cellulose (HPC) and mixtures thereof.

In one embodiment the non-ionic cellulose derivative comprises HPC. There are a number of different grades of HPCs available commercially of varying degrees of polymerisation and molecular weight. Suitably grades of HPC having an average molecular weight (M.W.) falling within the range of from about 80,000 to about 370,000 may be used, such as from about 90,000 to about 150,000. Suitable examples include those that are available commercially as Klucel GF (M.W.≈370,000), Klucel JF (M.W.≈140,000), Klucel LF (M.W.≈95,000) and Klucel EF (M.W.≈80,000), available from Hercules Incorporated, Aqualon Division, Hercules Plaza, 1313 North Market Street, Wilmington, Del. 19894-0001, USA. Suitably the non-ionic polymer for use in the invention is used in an amount ranging from 0.1 to 10% by weight of the composition, such as 1 to 5%.

WPI Abstract Accession No. 2000-518334/47 and JP2000178151A disclose oral compositions containing one or more salts selected from sodium sulphate, magnesium chloride, sodium chloride, and potassium chloride, and at least one cellulosic polymer selected from hydroxyethyl methylcellulose, hydroxypropylmethylcellulose, and ethylhydroxyethylcellulose. The compositions are disclosed for use in cleaning oral cavities. There is no disclosure or suggestion that such compositions exhibit a cloudy phase at body temperature, or that they may be used for combating dentine hypersensitivity.

Whilst EP 0 558 586 B1 discloses compositions comprising a water-soluble, non-ionic cellulose ether having a cloud point no higher than 40° C., such compositions are not suitable for use herein. The compositions according to EP 0 558 586B 1 are characterized in that they comprise a water-soluble non-ionic cellulose ether having a cloud point not higher than 40° C., preferably not higher than 35° C., a charged surfactant, and optional additives in water. The compositions therein form a gel and exhibit an increase in viscosity when warmed to body temperature. According to EP 0 558 586B 1 the origin of the gel resides in the presence in the composition of the polymer in combination with the charged surfactant and the strong hydrophobic interactions between the two which are cooperative in nature and resemble normal micelle formation. In contrast, a composition according to the present invention does not form a gel and exhibits a decrease in viscosity when warmed to body temperature. A composition according to the present invention is essentially free of a charged surfactant. By "essentially free" is meant that there is either no charged surfactant present or if present, is present only in a small amount insufficient to cause gelling of the composition when warmed to body temperature. In one embodiment according to the invention a composition is free of any charged surfactant. In an alternative embodiment in which a small amount of charged surfactant may be tolerated, the ratio of such surfactant to the non-ionic polymer is at least 1:40, for example from 1:40 to 1:100.

By "cloud point" (CP) is meant the temperature at which a transparent aqueous solution of the non-ionic polymer becomes cloudy and bulk phase separation occurs.

Whilst not being bound by any theory, phase separation occurs when polymer-water interactions become less favourable, for example as may occur when temperature is increased e.g. from room temperature to body temperature. Cloud point may be visually determined by observing the temperature at which an aqueous solution of the non-ionic polymer becomes cloudy or turbid. Alternatively since phase separation results in a lowering of viscosity, rheological techniques may also be employed to determine cloud point. For example by carrying out a temperature-viscosity sweep using an Anton-Paar air bearing rheometer utilising a 50 mm diameter parallel plate (with vapour trap) with 0.3 mm gap, 20/s shear rate and a temperature ramp from 20° C.-45° C. At room temperature a composition according to the invention is in the form of a homogenous liquid whilst at oral body temperature, that is at about 37° C., the composition undergoes a phase transition to form a two-phase cloudy system with one phase dispersed in the other. In order to be in the form of a homogenous liquid at room temperature or below and in the form of a two-phase cloudy system at body temperature, the non-ionic polymers of use in the invention have a CP in the composition no higher than 39° C. or about 38° C. In one embodiment the non-ionic polymer exhibits a cloud point in the range of about 32° C. to about 38° C.

In one aspect a composition according to the invention comprises a cloud point modifying agent. A cloud point modifying agent can be used to shift the intrinsic CP of a non-ionic polymer to a desired temperature for example from about 45° C. to about 39° C. or below. By "intrinsic CP" is meant the CP in a simple aqueous solution. In one embodiment a cloud point modifying agent shifts the intrinsic CP from about 41° C. to about 32° C. Suitable cloud point modifying agents include agents that influence solvent quality such as salts or humectants.

Suitable salts for use herein include alkali metal salts such as a sodium salt e.g. sodium chloride and sodium citrate and mixtures thereof. In one embodiment the cloud point modifying agent comprises sodium citrate.

Suitably salts may be used in an amount ranging from 0.1 to 10%, typically from 0.5 to 5% by weight of the composition. In one embodiment an amount ranging from 0.1 to 1% by weight of the composition may be used.

In one aspect a composition of the invention may further comprise a humectant. Suitable humectants include those selected from glycerine, sorbitol, xylitol, propylene glycol or polyethylene glycol, or mixtures thereof. In one embodiment the humectant comprises glycerine. Suitably humectants may be used in an amount ranging from 1 to 40% by weight of the composition such as 1 to 30% by weight of the composition, typically from 2 to 15% by weight of the composition such as from 2 to 10% by weight of the composition.

Compositions of the present invention contain one or more orally acceptable carriers or excipients. Such carriers and excipients include appropriate formulating agents such as abrasives, surfactants, thickening agents, flavouring agents, sweetening agents, opacifying or colouring agents, pH buffering agents and preservatives, selected from those conventionally used in the oral care composition art for such purposes. Examples of such agents are as described in EP 929287 or WO6/013081.

Oral compositions of the present invention are typically formulated in the form of mouthwashes, sprays, or aqueous solutions for oral trays. In one embodiment the oral composition is in the form of a mouthwash. Compositions according to the present invention may be prepared by admixing the ingredients in the appropriate relative amount in any order that is convenient and if necessary adjusting the pH to give a desired value, for example from 4.0 to 9.5 e.g. from 5.5 to 9.0, such as from 6.0 to 8.0 or from 6.5 to 7.5.

The present invention also provides a method of combating dentine hypersensitivity which comprises applying an effective amount of a composition as herein before defined to an individual in need thereof.

The invention is further illustrated by the following Examples:

EXAMPLE 1

Rheology Assessment of HPC Solutions

The following aqueous solutions (Formulas 1-4) were prepared:

| Ingredient | Formula 1 % w/w | Formula 2 % w/w | Formula 3 % w/w | Formula 4 % w/w |
|---|---|---|---|---|
| HPC (Klucel JF) | 4.0 | 4.0 | 4.0 | 4.0 |
| Sodium Chloride | — | — | 4.0 | 0.50 |
| Glycerine | — | 20.0 | — | 5.0 |
| PEG-60 Hydrogenated Castor Oil | — | — | — | 1.0 |
| Flavour | — | — | — | 0.20 |
| Sodium Saccharin | — | — | — | 0.05 |
| Cetylpyridium Chloride | — | — | — | 0.05 |
| Methyl paraben | — | — | — | 0.05 |
| Propyl paraben | — | — | — | 0.05 |
| FD&C Blue No 1 | — | — | — | 0.0002 |
| Water | To 100 | To 100 | To 100 | To 100 |

Methods

The viscosity values were determined for Formulas 1-4 using an Anton-Paar air-bearing rheometer, using a 50 mm diameter parallel plate (with vapour trap) with 0.3 mm gap, 20/s shear rate and a temperature ramp of 20° C. to 45° C., following an initial settling period at 20° -30° C.

Results

The results of the effects of increasing temperature on the viscosity of aqueous solutions of HPC are shown in Table 1 below. The influence of the addition of salt and humectant on the viscosity is also shown.

TABLE 1

Temperature vs. Viscosity

| | Temperature ° C. | | | | | | | | |
|---|---|---|---|---|---|---|---|---|---|
| | 20.0 | 25.0 | 30.0 | 32.5 | 35.0 | 37.5 | 40.0 | 42.5 | 45.0 |
| Formula 1 (viscosity mPa · s) | 107 | 93 | 79 | 73 | 69 | 67 | 63 | 55 | 23 |
| Formula 2 (viscosity mPa · s) | 229 | 197 | 166 | 150 | 122 | 90 | 22 | 11 | 8 |
| Formula 3 (viscosity mPa · s) | 139 | 124 | 111 | 76 | 12 | 5 | 4 | 5 | 6 |
| Formula 4 (viscosity mPa · s) | 74 | 65 | 54 | 44 | 36 | 14 | 5 | 2 | 2 |

Conclusions

The viscosity of the solution containing polymer alone decreases slowly with temperature until around 42.5° C. when a significant drop is observed resulting from the polymer phase transition, upon reaching its cloud point. The other formulations show this viscosity drop at lower temperatures as a result of a shift in the cloud point and the corresponding phase transition resulting in precipitation of the polymer.

EXAMPLE 2

Visual Determination of Cloud Point

The following additional aqueous solutions (Formulas 5-12) were prepared:

| Ingredient | Formula 5 % w/w | Formula 6 % w/w | Formula 7 % w/w | Formula 8 % w/w | Formula 9 % w/w | Formula 10 % w/w | Formula 11 % w/w | Formula 12 % w/w |
|---|---|---|---|---|---|---|---|---|
| HPC (Klucel LF) | — | — | 2.0 | — | — | — | — | — |
| HPC (Klucel JF) | 2.0 | 4.0 | — | — | 4.0 | 4.0 | — | 2.0 |
| HPC (Klucel GF) | — | — | — | 1.0 | — | — | — | — |
| Sodium Chloride | 4.0 | 4.0 | 4.0 | 4.0 | 0.50 | 0.50 | 0.50 | 0.50 |
| Glycerine | — | — | — | — | 5.0 | 5.0 | 5.0 | 5.0 |
| PEG-60 Hydrogenated Castor Oil | — | — | — | — | 1.0 | 1.0 | 1.0 | 1.0 |
| Flavour | — | — | — | — | 0.20 | 0.20 | 0.20 | 0.20 |
| Sodium Saccharin | — | — | — | — | 0.05 | 0.05 | 0.05 | 0.05 |

-continued

| Ingredient | Formula 5 % w/w | Formula 6 % w/w | Formula 7 % w/w | Formula 8 % w/w | Formula 9 % w/w | Formula 10 % w/w | Formula 11 % w/w | Formula 12 % w/w |
|---|---|---|---|---|---|---|---|---|
| Cetylpyridium Chloride | — | — | — | — | — | 0.05 | — | — |
| Methyl paraben | — | — | — | — | — | 0.05 | — | — |
| Propylparaben | — | — | — | — | — | 0.05 | — | — |
| FD&C Blue No 1 | — | — | — | — | 0.0002 | 0.0002 | 0.0002 | 0.0002 |
| Water | To 100 | To 100 | To 100 | To 100 | To 100 | To 100 | To 100 | To 100 |

Cloud Point Determination

The cloud point was determined by equilibration of the samples in a water bath at the chosen temperatures. The samples were visually inspected and the temperature where the samples became turbid was recorded.

Results

The results are shown in Table 2 below.

TABLE 2

Cloud points for Formula Examples

| | | Observations | | | | | | |
|---|---|---|---|---|---|---|---|---|
| Formula | Mw HPC | 22° C. | 25° C. | 28° C. | 30° C. | 32° C. | 35° C. | 37° C. |
| 1 | 140000 | Clear | Clear | Clear | Clear | Clear | Clear | Clear |
| 2 | 140000 | Clear | Clear | Clear | Clear | Clear | Cloudy | Cloudy |
| 3 | 140000 | Clear | Clear | Clear | Clear | Cloudy | Cloudy | Cloudy |
| 4 | 140000 | Clear | Clear | Clear | Clear | Cloudy | Cloudy | Cloudy |
| 5 | 140000 | Clear | Clear | Clear | Clear | Cloudy | Cloudy | Cloudy |
| 6 | 140000 | Clear | Clear | Clear | Clear | Cloudy | Cloudy | Cloudy |
| 7 | 95000 | Clear | Clear | Clear | Clear | Cloudy | Cloudy | Cloudy |
| 8 | 370000 | Clear | Clear | Clear | Clear | Clear | Cloudy | Cloudy |
| 9 | 140000 | Clear | Clear | Clear | Clear | Clear | Cloudy | Cloudy |
| 10 | 140000 | Clear | Clear | Clear | Clear | Cloudy | Cloudy | Cloudy |
| 11 | N/A | Clear | Clear | Clear | Clear | Clear | Clear | Clear |
| 12 | 140000 | Clear | Clear | Clear | Clear | Clear | Cloudy | Cloudy |

Conclusions

The results show that when compared to the solutions containing no HPC or HPC alone the cloud points observed are lower. This occurs with a range of HPC concentrations and molecular weights and demonstrates the influence of the inclusion of the formula components.

EXAMPLE 3

Hydraulic Conductance

The Hydraulic Conductance (HC) of sample solutions (Formulas 5-11) was determined.

Methodology

Hydraulic conductance experiments were carried out at 35-36° C. and 70% relative humidity in order to simulate conditions in the oral cavity. Samples were applied at room temperature and then heated when in contact with the dentine disc surface. The reduction in the flow of Earles solution through the dentine disc following the baseline measurement, 3 subsequent treatments with test solutions and rinses with water. A treatment consisted of application of the test solution to the dentine disc and the hydraulic conductance being re-measured at one minute intervals (over a 5 minute time period). The mean value obtained was used to calculate a percentage permeability reduction for the particular test solution.

Results

The HC results are displayed below in Table 3. All samples were measured three times with three different dentin discs. The mean hydraulic conductance has been calculated for each treatment number and the value after the third treatment statistically compared relative to a composition containing no HPC.

TABLE 3

Hydraulic Conductance of Formula Examples

| Formula | Cloud Point Degrees C. | Treatment Number | Mean HC Reduction % (n = 3) | SE | p Value vs. Control Example 11 |
|---|---|---|---|---|---|
| 5 | 32 | 1 | 60 | 4.4 | |
| | | 2 | 78 | 5 | |
| | | 3 | 83 | 4.3 | 0.00145 |
| 6 | 32 | 1 | 43 | 1.5 | |
| | | 2 | 52 | 8.2 | |
| | | 3 | 57 | 2.7 | 0.00163 |
| 7 | 32 | 1 | 36 | 19.9 | |
| | | 2 | 68 | 4.9 | |
| | | 3 | 77 | 2.8 | 0.00146 |
| 8 | 35 | 1 | 52 | 8.1 | |
| | | 2 | 63 | 12.6 | |
| | | 3 | 75 | 2.9 | 0.00178 |
| 9 | 35 | 1 | 57 | 9 | |
| | | 2 | 66 | 6.7 | |
| | | 3 | 82 | 7.5 | 0.00470 |
| 10 | 32 | 1 | 53 | 8.3 | |
| | | 2 | 73 | 7 | |
| | | 3 | 73 | 2.0 | 0.00165 |
| 11 (Control) | NA | 1 | 25 | 8.7 | |
| | | 2 | 27 | 11 | |
| | | 3 | 29 | 5.5 | NA |
| 12 | 35 | 1 | 71 | 8.1 | |
| | | 2 | 77 | 4.1 | |
| | | 3 | 80 | 6.2 | 0.00367 |

The results show that the solutions, which all have reduced cloud points have corresponding high levels of hydraulic conductance reduction, significantly ($p \leq 0.05$) different from the control.

The invention claimed is:

1. An oral care composition which is a transparent aqueous solution at or below room temperature and which forms a two-phase cloudy system at body temperature and wherein the composition consists essentially of:
   1) hydroxypropyl cellulose having an average molecular weight of about 95,000 to about 370,000 in an amount of from 1 to 5% by weight of the composition and wherein the hydroxypropyl cellulose has a cloud point in the composition at a temperature no higher than about 38° C., and
   2) one or more cloud point modifying agents selected from an alkali metal salt in an amount from 0.5 to 5% by weight of the composition or a humectant which is selected from glycerine, sorbitol, propylene glycol or polyethylene glycol or a mixture thereof, in an amount from 2 to 15% by weight of the composition; and
   3) water in an amount up to 100% by weight of the composition.

2. A composition according to claim 1 wherein the nonionic polymer in the composition has a cloud point in the range 32° to 38° C.

3. A composition according to claim 1 wherein the salt comprises sodium citrate.

4. A composition according to claim 1 wherein the humectant is present in an amount ranging from 2 to 10% by weight of the composition.

5. A composition according to claim 1 wherein the humectant comprises glycerine.

6. A composition according to claim 1 wherein the hydroxypropyl cellulose is selected from Klucel GF (M.W.≈370,000), Klucel JF (M.W.≈140,000), Klucel LF (M.W.≈95,000) and Klucel EF (M.W.≈80,000).

7. A composition according to claim 6 wherein the hydroxypropyl cellulose comprises Klucel JF.

8. A composition according to claim 1 wherein the nonionic polymer is present in an amount ranging from 1 to 5% by weight of the composition.

9. A method of treating dentine hypersensitivity comprising administering a composition according to claim 1.

* * * * *